United States Patent
Urie (12)

(10) Patent No.: US 12,005,190 B2
(45) Date of Patent: Jun. 11, 2024

(54) NASAL CANNULA

(71) Applicant: Mediplus Ltd, Buckinghamshire (GB)

(72) Inventor: Robert Graham Urie, Buckinghamshire (GB)

(73) Assignee: Mediplus Ltd, Buckinghamshire (GB)

( * ) Notice: Subject to any disclaimer, the term of this patent is extended or adjusted under 35 U.S.C. 154(b) by 703 days.

(21) Appl. No.: 17/042,456

(22) PCT Filed: Mar. 27, 2019

(86) PCT No.: PCT/GB2019/050874
§ 371 (c)(1),
(2) Date: Sep. 28, 2020

(87) PCT Pub. No.: WO2019/186155
PCT Pub. Date: Oct. 3, 2019

(65) Prior Publication Data
US 2021/0023322 A1     Jan. 28, 2021

(30) Foreign Application Priority Data

Mar. 29, 2018   (GB) ...................................... 1805214

(51) Int. Cl.
*A61M 16/06*      (2006.01)
*A61M 16/08*      (2006.01)

(52) U.S. Cl.
CPC ...... *A61M 16/0672* (2014.02); *A61M 16/085* (2014.02); *A61M 2202/0208* (2013.01); *A61M 2202/0225* (2013.01); *A61M 2230/43* (2013.01)

(58) Field of Classification Search
CPC ............ A61M 16/0672; A61M 16/085; A61M 2202/0208; A61M 2202/0225; A61M 2230/43; A61M 2205/21
See application file for complete search history.

(56) References Cited

U.S. PATENT DOCUMENTS

| 3,802,431 A | 4/1974 | Farr |
| 6,561,192 B2 * | 5/2003 | Palmer .............. A61M 16/0488 |
| | | 128/207.14 |

(Continued)

FOREIGN PATENT DOCUMENTS

| CN | 203710512 U | 7/2014 | |
| WO | WO 8909565 A1 * | 4/1989 | ............. A61B 5/097 |

(Continued)

OTHER PUBLICATIONS

International Search Report and Written Opinion for corresponding International Patent Application No. PCT/GB2019/050874 mailed on Jul. 3, 2019.

(Continued)

*Primary Examiner* — Samchuan C Yao
*Assistant Examiner* — Tina Zhang
(74) *Attorney, Agent, or Firm* — Renner, Otto, Boisselle & Sklar, LLP (57) ABSTRACT

A nasal cannula comprises a body portion, having a first end and a second end spaced from the first end by the body portion; a body fluid inlet port formed at the first end, and a body fluid outlet port formed at the second end; and a first nasal inlet port and a first nasal outlet port each extending from the body portion of the cannula. The first nasal inlet port is in fluid communication with the body fluid outlet port, and the first nasal outlet port is in fluid communication with the body fluid inlet port. The nasal cannula includes first and second end caps at the first and second ends respectively. The first and second end caps are attachable to the body portion. The body fluid inlet port is formed in the first end cap, and the body fluid outlet port is formed in the second end cap.

12 Claims, 10 Drawing Sheets

(56) References Cited

U.S. PATENT DOCUMENTS

| | | | |
|---|---|---|---|
| 9,393,375 B2* | 7/2016 | Hernandez | A61M 16/0633 |
| 10,610,653 B2* | 4/2020 | Spence | A61M 16/16 |
| 2006/0130840 A1* | 6/2006 | Porat | A61M 16/0666 |
| | | | 128/207.18 |
| 2007/0107737 A1* | 5/2007 | Landis | A61M 16/0672 |
| | | | 128/207.18 |
| 2007/0113856 A1 | 5/2007 | Acker et al. | |
| 2014/0130805 A1* | 5/2014 | Tiep | A61M 16/0683 |
| | | | 128/207.18 |
| 2014/0150789 A1 | 6/2014 | Flanagan et al. | |
| 2016/0213281 A1* | 7/2016 | Eckerbom | A61M 16/085 |
| 2017/0007794 A1* | 1/2017 | Atherton | A61M 16/125 |

FOREIGN PATENT DOCUMENTS

| | | |
|---|---|---|
| WO | 89/09565 | 10/1989 |
| WO | 2012/037469 | 3/2012 |
| WO | 2016/118922 | 7/2016 |

OTHER PUBLICATIONS

Combined Search and Examination Report issued Oct. 2, 2018, for corresponding application No. GB1805214.2.

\* cited by examiner

NASAL CANNULA

RELATED APPLICATIONS

This application is a national phase of International Application No. PCT/GB2019/050874, filed Mar. 27, 2019, which claims benefit of GB Patent Application No. 1805214.2, filed on Mar. 29, 2018, and published in the English language.

FIELD OF THE INVENTION

This invention relates to a nasal cannula, and particularly, but not exclusively to a nasal cannula used to deliver oxygen to a patient.

BACKGROUND OF THE INVENTION

It is known in the art that a nasal cannula may be used to deliver a fluid, usually supplemental oxygen to a patient. Such a cannula may also be used to measure levels of carbon dioxide exhaled from a patient using the cannula.

A known nasal cannula comprises a body portion which is generally tubular in shape together with two projections, or prongs which are adapted to be placed in the nostrils of a patient. The cannula enables oxygen to be delivered to the patient via the nostrils of a patient, and carbon dioxide that has been exhaled by the patient to be removed and/or measured.

It is necessary to attach such a cannula to a supply of the fluid to be delivered, such as a supply of oxygen, on the one hand, and to an outlet conduit for removing fluid such as exhaled carbon dioxide from the vicinity of the patient.

SUMMARY OF THE INVENTION

According to a first aspect of the present invention there is provided a nasal cannula comprising:
  a body portion, having a first end and a second end, the first and second ends being spaced apart from one another, by the body portion;
  a body fluid inlet port formed at the first end, and a body fluid outlet port formed at the second end; and
  a first nasal inlet port and a first nasal outlet port each extending from the body portion of the cannula, the first nasal inlet port being in fluid communication with the body fluid outlet port, and the first nasal outlet port being in fluid communication with the body fluid inlet port,
  wherein the nasal cannula comprises first and second end caps at the first and second ends respectively, which first and second end caps are attachable to the body portion, and wherein the body fluid inlet port is formed in the first end cap, and the body fluid outlet port is formed in the second end cap.

The first and second end caps facilitate the manufacture of the nasal cannula and enable the end caps to be made from a different material to the material used to make the body of the cannula, but in some embodiments of the invention the end caps are made from the same material as the material used to the make the body of the cannula.

In some embodiments of the invention, the end caps are made from a material that is harder than the material used to make the body of the cannula. In such embodiments, the production and assembly of the cannula is facilitated.

In some embodiments of the invention, the body portion may be made from a medical grade polymer such as PVC or polyurethane, although other polymers could also be used.

In some embodiments of the invention the end caps are made from polycarbonate or ABS. These materials are harder than polymers such as PVC and polyurethane.

In some embodiments of the invention, the nasal cannula will be used to supply oxygen to a patient and therefore the first end cap will be attachable to a conduit attached to a supply of oxygen. The nasal cannula will generally be used to remove exhaled air from the patient and therefore the outlet conduit will deliver exhaled air to a suitable location.

The nasal cannula may further comprise a plate extending from the middle body portion of the nasal cannula.

According to a second aspect of the present invention there is provided a nasal cannula comprising:
  a body portion, having a first end and a second end, the first and second ends being spaced apart from one another by the body portion;
  a body fluid inlet formed at the first end, and a body fluid outlet formed at the second end; and
  a first nasal inlet port and a first nasal outlet port each extending from the body portion of the cannula, the first nasal inlet port being in fluid communication with the body fluid outlet port, and the first nasal outlet port being in fluid communication with the body fluid inlet port,
  wherein the nasal cannula further comprises a plate extending from the body portion.

The plate may serve to stabilise the position of the nasal cannula when in use. In particular the plate may prevent the nasal cannula from rolling and/or twisting in use.

In use, the plate may extend from a back surface of the middle body portion of the cannula, such that it is in contact with, or close to the skin of a patient during use of the cannula.

The body portion of the nasal cannula may be generally tubular, although it may have other shapes as appropriate.

In embodiments of the invention the first and second caps are each angled relative to the body portion.

The term "angled" is used herein to denote that the first and second end caps each extend along an axis that is not the same axis as an axis along which the body portion extends.

In other words, the first and second end caps will each extend along an axis which axis will intersect the axis of the body portion at an angle that is greater than zero and less than 180°.

In other embodiments however, the first and second caps extend axially from the body portion and are therefore substantially co-axial with the body portion.

The first and second end caps may be attached to the body portion by any convenient means, such as by means of an adhesive.

In some embodiments of the invention, the first and second end caps comprise a first and second spigot respectively, which spigot is shaped to fit into a hollow end of the body portion.

In such embodiments of the invention, the body fluid inlet port and the body fluid outlet port may each comprise an elongate portion extending from a respective end cap.

The elongate portion may take any convenient form, and may for example be in the form of a nozzle or spike.

In embodiments of the invention the nasal cannula comprises a second nasal inlet port and a second nasal outlet port, each extending from the body portion of the cannula, the second nasal input port being in fluid communication with the body fluid outlet port, and the second nasal outlet port being in fluid communication with the body fluid inlet port.

In embodiments of the invention the first nasal inlet port and the first nasal outlet port are formed within a first nasal projection extending from the body portion, and the second nasal inlet port and second nasal outlet port are formed within a second nasal projection extending from the body portion, which second nasal projection is spaced apart from the first nasal projection.

In such embodiments of the invention the plate may extend in a direction that is generally opposite to the direction in which the first and second nasal projections extend from the body portion.

In use, the nasal projections may extend generally upwardly, whilst the plate will extend generally in a downward direction.

In use, the nasal projections will be inserted into the nostrils of a patient, with the body portion of the nasal cannula extending generally below the nose of the patient to which the cannula has been fitted. The plate will extend below the cannula body to provide stability to the nasal cannula.

In embodiments of the invention the nasal cannula comprises an inlet lumen extending from the body inlet port to the first and second nasal outlet ports, and an outlet lumen extending from the first and second nasal inlet ports to the body outlet port.

The inlet and outlet lumens may have any particular size or shape suitable for the application to which the nasal cannula is to be put.

In embodiments of the invention each nasal projection may comprise an outlet channel extending from the outlet lumen, and an outlet channel extending to the outlet lumen, the inlet channel and the outlet channel each extending longitudinally through a respective nasal projection.

In such embodiments of the invention the input lumen extends from the body inlet port to the outlet channel, and the outlet lumen extends from the body outlet port to the inlet channel.

In embodiments of the invention the cannula may comprise a divider extending through the body portion and longitudinally at least pivotally through which divider, together with the walls of the nasal projections, and the walls of the body portion, defines the inlet channels and the outlet channel, the inlet lumen and the outlet lumen.

The first and second nasal projections may take any form, but in embodiments of the invention each nasal projection comprises a prong extending from a surface of the body portion.

Each prong may extend longitudinally in a substantially straight manner. In other embodiments of the invention each projection may be curved, longitudinally.

In embodiments of the invention each nasal projection comprises a proximal portion and a distal portion, whereby each inlet channel extends through the proximal portion and the distal portion of a respective projection, and each outlet channel extends through a proximal portion only of a respective projection.

In such embodiments of the invention, the proximal portion of each projection is the portion of a nasal projection that is closest to the body portion of the nasal cannula.

In such embodiments of the invention, each nasal projection may have a stepped contour. The proximal portion may be substantially tubular, and the distal portion of the nasal projection may have a substantially semi-circular cross-section.

The first and second nasal projections will generally be substantially identical to one another, although in some embodiments of the invention the first nasal projection may have a different size and/or shape to the second nasal projection.

The first and second nasal projections will be spaced apart by a distance that allows the nasal cannula to be fitted to a patient such that each nasal projection may be inserted into a nostril of the patient.

BRIEF DESCRIPTION OF THE DRAWINGS

The invention will now be further described by way of example only with reference to the accompanying drawings in which.

DETAILED DESCRIPTION

Referring initially to FIGS. 1 to 4, a nasal cannula according to a first embodiment of the invention is designated generally by the reference numeral 2. The nasal cannula comprises a body portion 4 having a first end 6 and a second end 8. The ends 6, 8 are spaced apart from one another by the body portion 4. The nasal cannula 2 comprises a body fluid inlet port 12 formed at the second end 8, and a body fluid outlet port 14 formed at the first end 6.

The nasal cannula 2 further comprises a first nasal input port 16, and a first nasal outlet port 18 extending from the body portion 4 of the cannula. The nasal cannula 2 further comprises a second nasal inlet port 20 and a second nasal outlet port 22 each extending from the body portion 4 of the cannula 2. The first and second nasal inlet ports 16, 20 are in fluid communication with the body fluid outlet port 14, and the first and second nasal outlet ports 18, 22 are in fluid communication with the body fluid inlet port 12.

The nasal cannula 2 further comprises first and second end caps 24, 26 formed at the first and second ends 6, 8 respectively. These first and second end caps 24, 26 are attached to the body portion 4 by any convenient means. The body fluid inlet port 12 is formed in the second end cap 26 and the body fluid outlet port 14 is formed in the first end cap 24.

In this embodiment of the invention, the end caps 24, 26 are angled relative to the body portion 4 of the cannula 2. In other words, the end caps 24, 26 do not extend coaxially with the body portion 4, but extend at an angle that is not zero or 180° to the axis of the middle portion 10.

The first nasal inlet port 16 and the first nasal outlet port 18 are formed in a first nasal projection 28, and the second nasal inlet port 20 and the second nasal outlet port 22 are formed in a second nasal projection 30.

In this embodiment of the invention each of the nasal projections 28, 30, curves longitudinally away from the body portion 4.

The nasal cannula 2 further comprises a plate 32 extending from the body portion 4. The plate 32 extends in a direction that is generally opposite to the direction in which the first and second nasal projections 28, 30, project.

The plate 32 is attached to the body portion 4 of the cannula 2. In this embodiment, the plate is attached to a rear surface 34 of the body portion 4. When the cannula 2 is in use, the first and second nasal projections 28, 30 will be inserted into nostrils of a patient, and the plate 32 will generally lie flat against the skin of a patient in an area below the nose of the patient. The plate 32 in use will generally extend downwardly away from the body portion 4 of the nasal cannula 2, whilst the first and second nasal projections 28, 30 will extend generally upwardly away from the body 4 during use of the cannula.

The first nasal projection 28 comprises a proximal portion 36 and a distal portion 38. Similarly, the nasal projection 30 comprises a proximal portion 40 and a distal portion 42.

Figure 1:
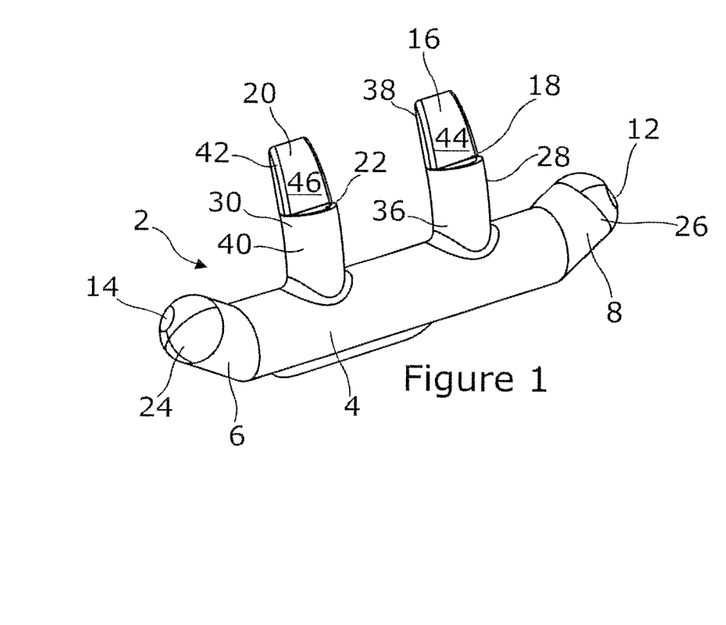
FIG. 1 is a schematic representation of a nasal cannula according to a first embodiment of the invention.
Figure 2:
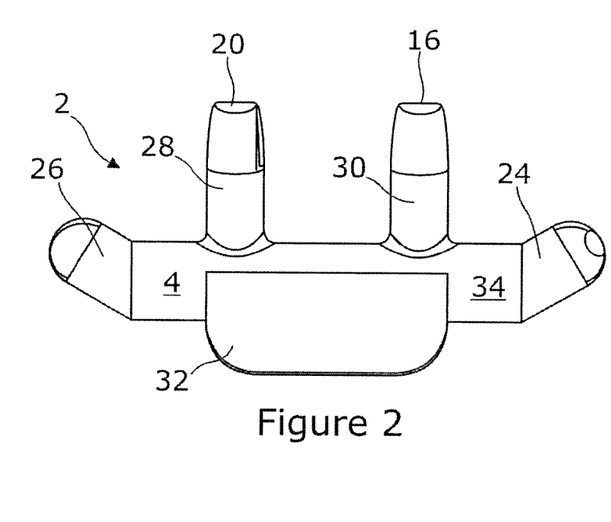
FIG. 2 is a back view of the nasal cannula of FIG. 1.
Figure 3:
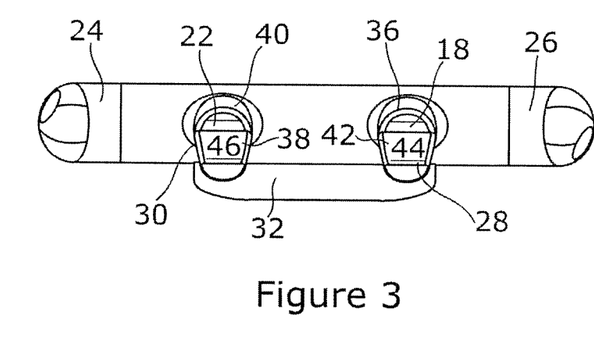
FIG. 3 is a view from above of the nasal cannula of FIG. 1.
Figure 4:
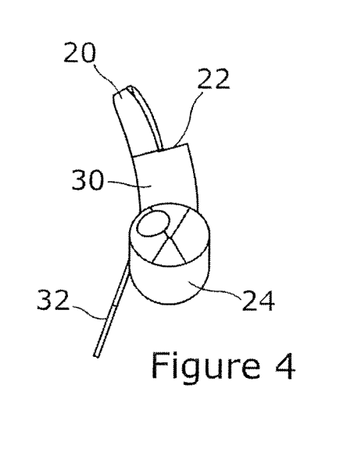
FIG. 4 is view from one side of the cannula of FIG. 1.
Figure 5:
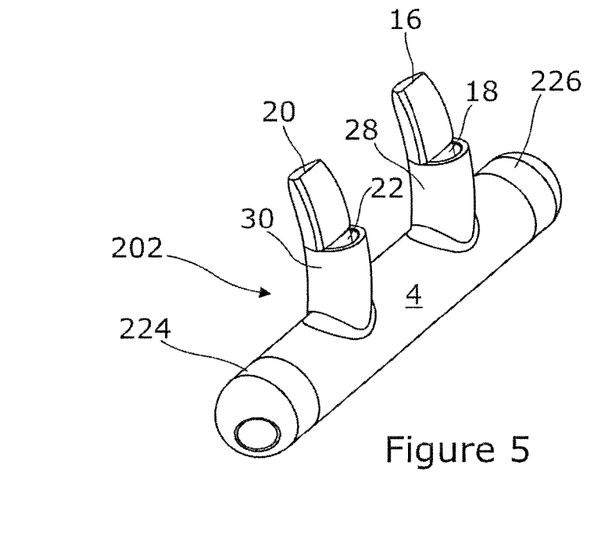
FIG. 5 is a schematic representation of a nasal cannula according to a second embodiment of the invention.
Figure 6:
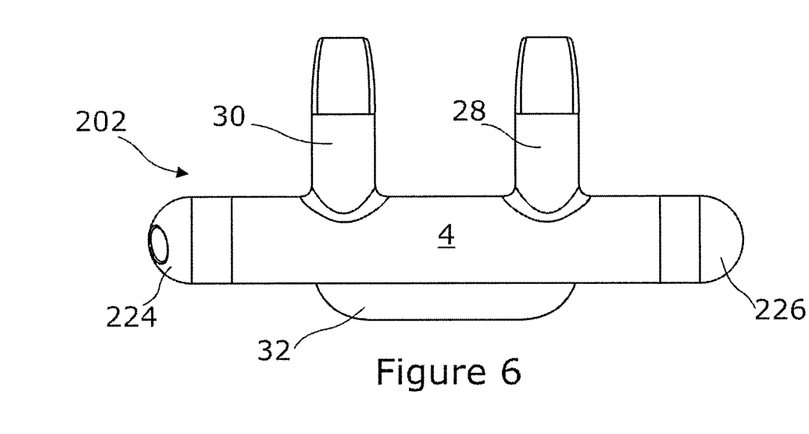
FIG. 6 is a front view of the nasal cannula of FIG. 5.
Figure 7:
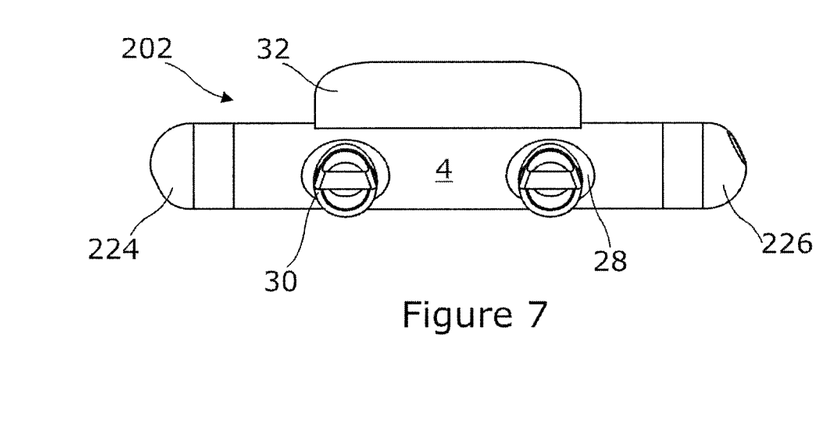
FIG. 7 is a view from above of the cannula of FIG. 5.
Figure 8:
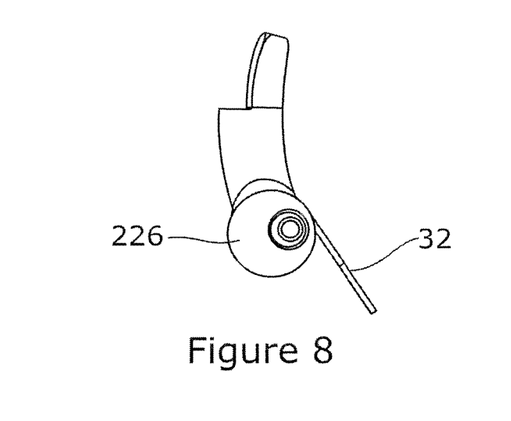
FIG. 8 is a view from one side of the cannula of FIG. 5.
Figure 9:
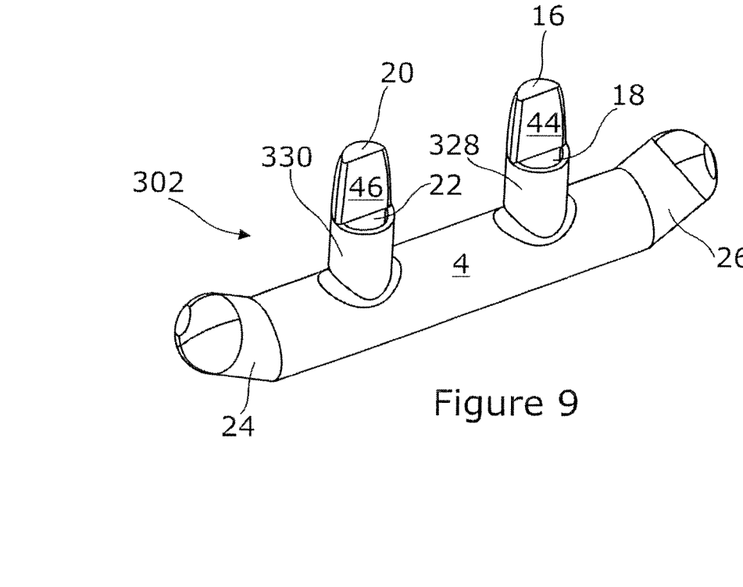
FIG. 9 is a schematic representation of a nasal cannula according to a third embodiment of the invention.
Figure 10:
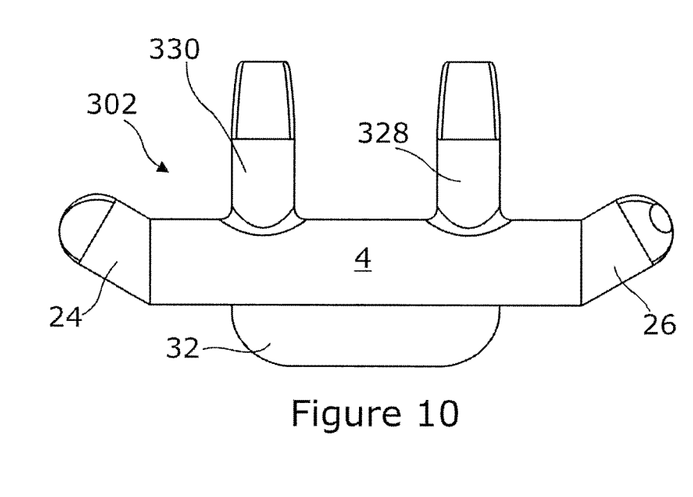
FIG. 10 is a front view of the nasal cannula of FIG. 9.
Figure 11:
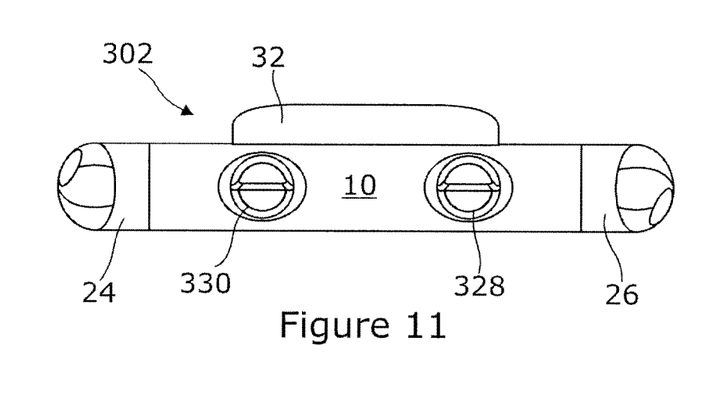
FIG. 11 is a view from above of the cannula of FIG. 9.
Figure 12:
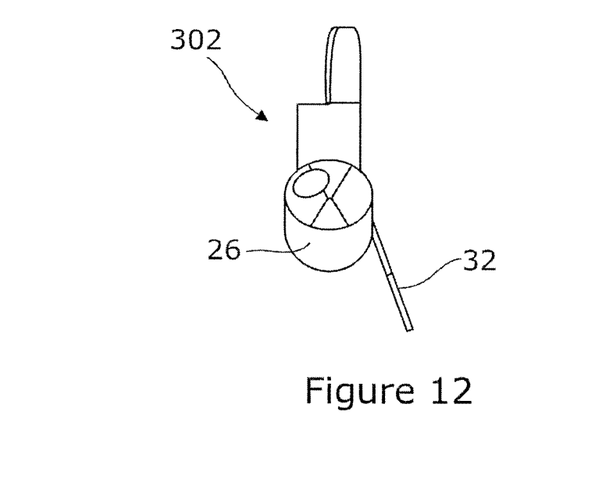
FIG. 12 is a view from one side of the cannula of FIG. 9.
Figure 13:
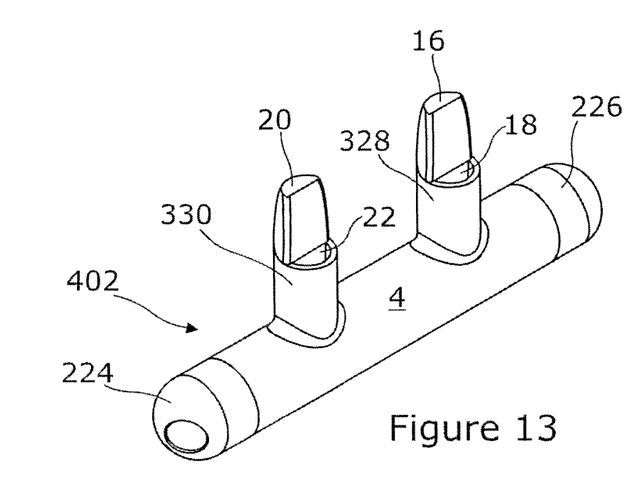
FIG. 13 is a schematic representation of a nasal cannula according to a fourth embodiment of the invention.
Figure 14:
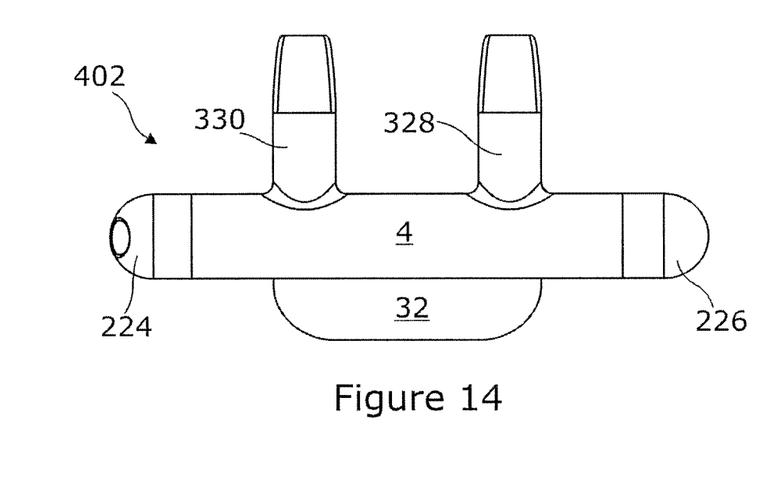
FIG. 14 is a front view of the nasal cannula of FIG. 13.
Figure 15:
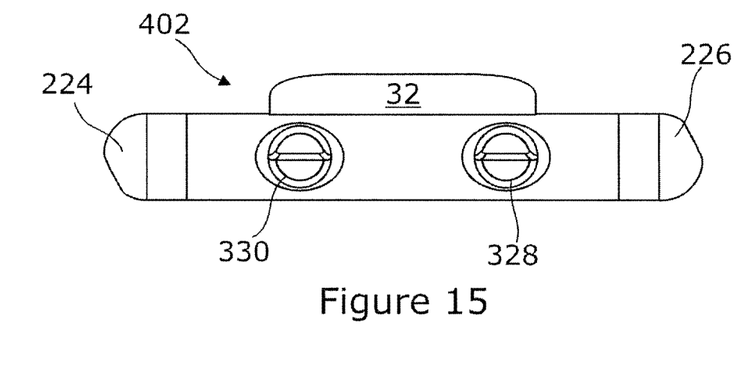
FIG. 15 is a view from above of the nasal cannula of FIG. 13.
Figure 16:
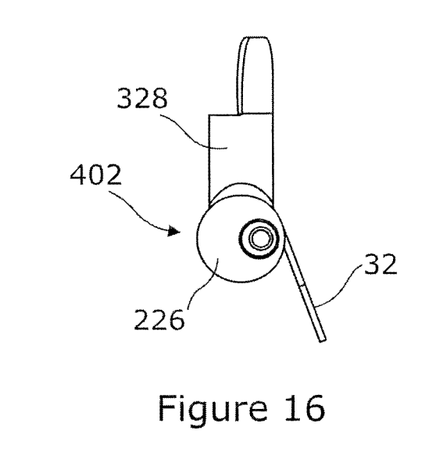
FIG. 16 is a view from one side of the nasal cannula of FIG. 13.

In this embodiment of the invention each proximal portion 36, 40 is substantially tubular in shape, and each distal portion 38, 42 is substantially semi-circular in cross-sectional shape as shown particularly in FIG. 3. Each nasal projection 28, 30 is therefore stepped as shown in the drawings, with each distal portion 38, 42 having a substantially flat surface 44, 46 respectively. Such a configuration means that the nasal inlet ports 16, 20 will be positioned further inside a patient's nostrils than will the first and second nasal outlet ports 18, 22.

An advantage of this configuration is that it helps to reduce so called washout during use of the cannula. Washout is the dilation of the exhaled breath with the incoming flow of oxygen. Washout can result in inaccurate readings being taken of the amount of carbon dioxide in the exhaled breath. By means of the stepped nasal projection 28, 30, these readings may be more reliable.

In addition, such a configuration can facilitate the inhalation of oxygen supplied via the first and second nasal outlet ports 18, 22 by a patient to which the cannula 2 has been fitted. Similarly, exhaled air containing carbon dioxide may be readily directed through the first and second nasal inlet ports 16, 20 2 to be removed from the patient and/or measured.

The first and nasal projections 28, 30 are spaced apart by a distance that is a similar distance to the distance between the nostrils of a patient. The cannula 2 may be manufactured in different sizes to suit different sizes of patient. For example, a cannula 2 that is to be fitted to a young child will have more closely spaced nasal projections 28, 30 than a cannula 2 that is to be fitted to an adult.

The plate 32 serves to stabilise the cannula 2 during use of the cannula. In use, the plate will lie on or close to the skin of a patient using the cannula 2. The plate 32 will help to prevent twisting or rolling motion of the cannula during use of the cannula.

Turning now to FIGS. 5 to 8, a cannula according to a second embodiment of the invention is designated generally by the reference numeral 202. Parts of the cannula 202 that correspond to parts of the cannula 2 illustrated in FIGS. 1 to 4 have been given corresponding reference numerals for ease of reference.

In this embodiment of the invention, the cannula 202 comprises end caps 224 and 226. The end caps extend axially from the body portion 4 and are not therefore angled relative to the body portion 4 as are the end caps 24, 26 in the cannula 2 according to the first embodiment of the invention.

Turning now to FIGS. 9 to 12, a cannula according to a third embodiment of the invention is designated generally by the reference numeral 302. Parts of the cannula that correspond to parts of the cannulas 2, 202 have been given corresponding reference numerals for ease of reference.

In this embodiment, the cannula 302 comprises nasal projections 328 and 330 that extend in a substantially straight in a longitudinal direction. In other words, the nasal projections 328, 330 are not curved longitudinally as is the case in cannulas 2 and 302. The cannula 302 further comprises end caps 24, 26 of the type shown with reference to the cannula 2 and illustrated in FIG. 1, for example.

Referring now to FIGS. 13 to 16, a cannula 402 according to a fourth embodiment of the invention will be described. Parts of the cannula 402 which correspond to parts of the cannulas 2, 202 and 302 have been given corresponding reference numerals for ease of reference.

In this case the cannula 402 comprises substantially straight nasal projections 328, 330, and end caps 224, 226 that extend axially from the body portion 4.

Use of a nasal cannula according to the embodiments of the invention will now be further described with particular reference to FIGS. 17 to 21.

Figure 17:
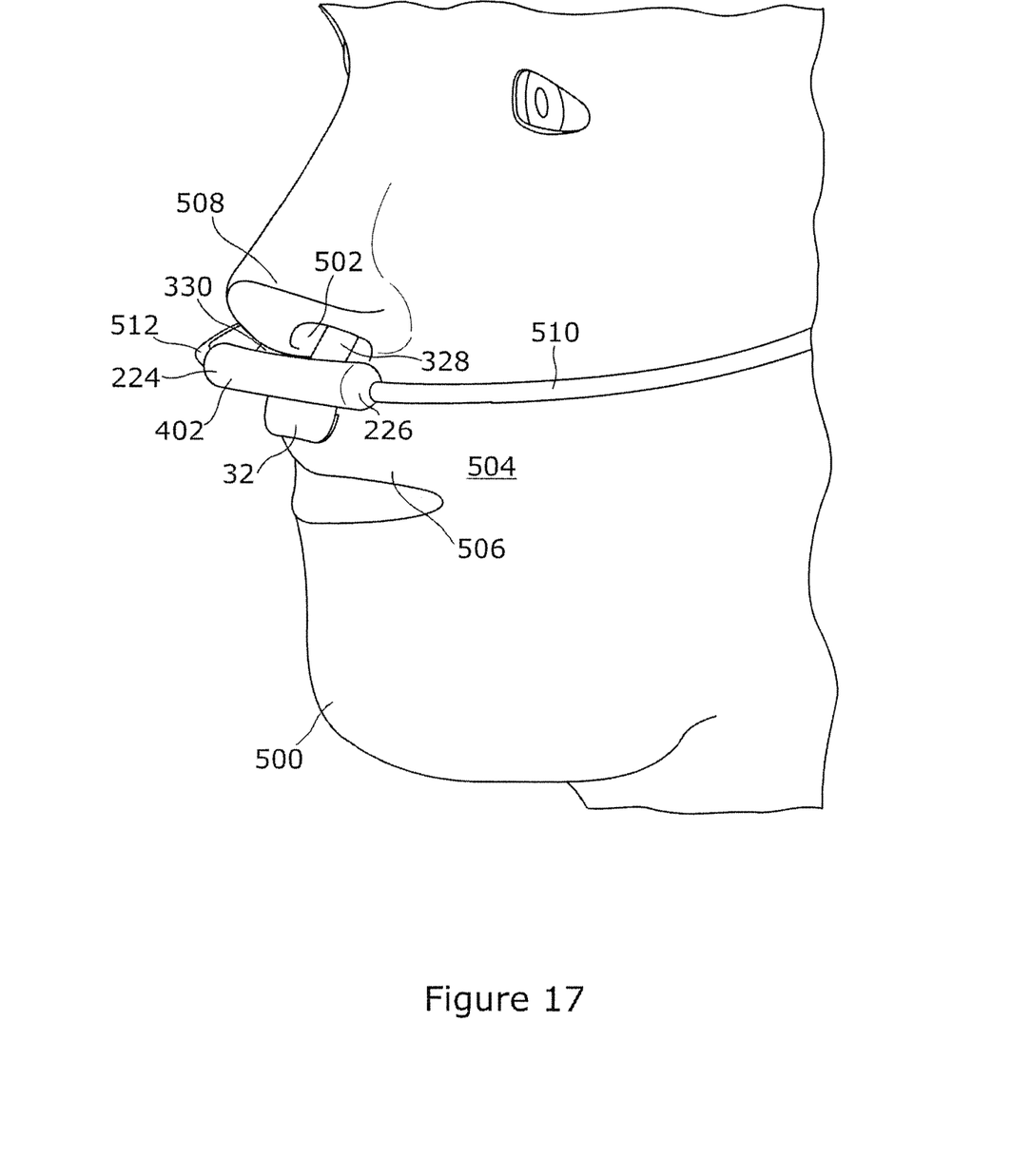
FIG. 17 is a schematic representation of a nasal cannula according to the fourth embodiment of the invention as illustrated in FIGS. 13 to 16, shown fitted to a patient.

Referring first to FIG. 17, a nasal cannula 402 of the type described herein above with reference to FIGS. 13 to 16, is shown fitted to a patient 500.

When the cannula 402 is fitted to the patient 500, the first and second nasal projections 328 and 330 are inserted into the nostrils 502 of the patient 500, and remain positioned within the nostrils 502 during use of the cannula 402.

When in position, the plate 32 rests against the face 504 of the patient and is positioned above the lips 506 and below the nose 508 of the patient.

An input conduit 510 is connected to the cannula 402 via endcap 226, and an outlet conduit 512 is connected to the nasal cannula 402 via endcap 224.

The input conduit 510 supplies oxygen to the patient 500, and the output conduit 512 removes exhaled air from the patient as will be described in more detail herein below with reference to FIG. 18.

Figure 18:
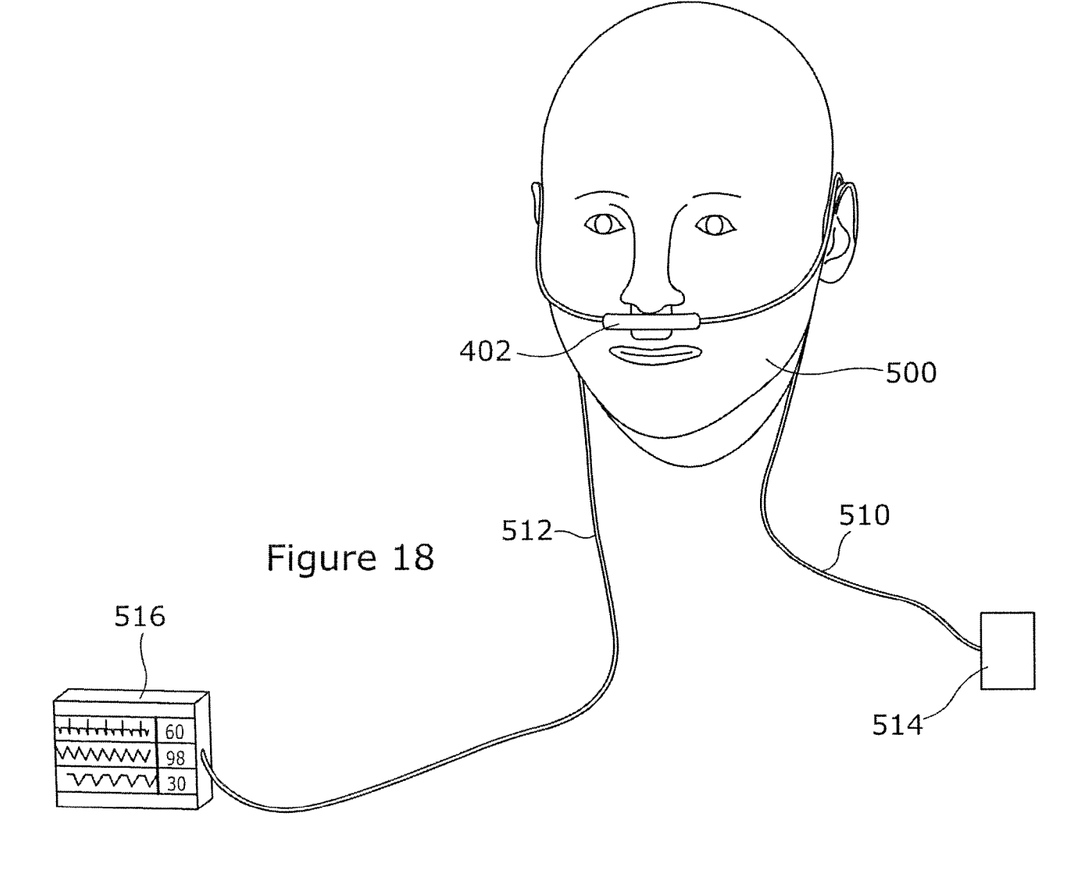
FIG. 18 is a schematic representation of the nasal cannula of FIG. 17 showing the device connected to a monitor and to a source of oxygen.

As can been seen from FIG. 18, the input conduit 510 is connected to an oxygen source 514, and the output conduit 512 is connected to a monitor 516.

During use of the cannula 402, oxygen is supplied to the patient 500 by means of the input conduit 510 connected to the oxygen source 514. Air that is exhaled by the patient 500 is then carried by the output conduit 512 to the monitor 516. The monitor 516 may measure various parameters, but particularly measures the amount of carbon dioxide in the exhaled air. The monitor may also be used to monitor heart rate and oxygen saturation levels, for example.

The internal structure of the nasal cannula 302 will now be further described with reference to FIGS. 19 to 20.

Figures 19, 20:
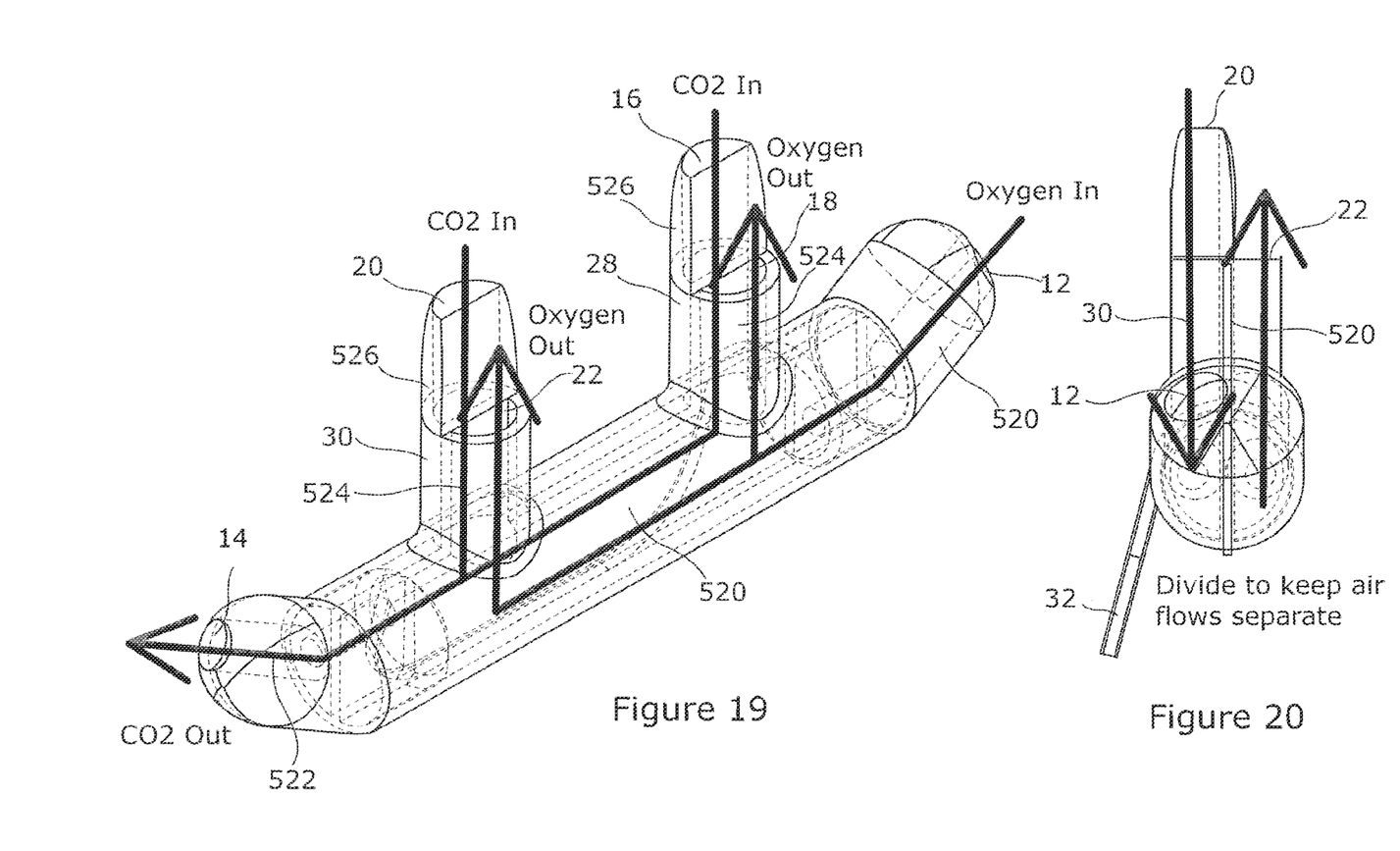
FIG. 19 is a schematic representation of a nasal cannula in accordance with the third embodiment of the invention as shown in FIGS. 9 and 12, showing flow of oxygen and carbon dioxide into and out of the nasal cannula.
FIG. 20 is a more detailed cross-sectional representation of part of the nasal cannula shown in FIG. 19 showing the structure of one of the nasal projections forming part of the nasal cannula.

Referring first to FIG. 19, the cannula 302 comprises inlet port 14 and outlet port 12.

Input conduit 510 is connected to the body fluid input port 12, and output conduit 512 is connected to the body fluid outlet port 14.

The nasal cannula 302 further comprises an input lumen 520 extending from the body fluid inlet port 12 towards the first and second nasal outlet ports 18, 22. The nasal cannula 302 further comprises an output lumen 522 extending to the body fluid outlet port 14.

In this embodiment of the invention each nasal projection 28, 30 comprises an outlet channel 524 extending between the input lumen 520 and a respective nasal outlet port 18, 22, and inlet channel 526 extending from a respective nasal inlet port 16, 20 to the output lumen 522 to the outlet port 12.

The inlet channel 524 and the outlet channel 526 each extend substantially longitudinally through a respective nasal projection.

The cannula 302 further comprises a divider 520 which extends through the body portion 4 and into each nasal projection. The divider 520, together with the walls of the respective nasal projections, and the walls of the body portion defines the inlet channel, the outlet channel, the input lumen and the output lumen. In other words, the divider serves to separate air flows within the cannula 402.

During use of the cannula 2, 202, 302, 402, oxygen from the oxygen supply 514 enters the cannula via the input port 14 via input conduit 510. The oxygen is then guided towards the first and second nasal outlet ports 18, 22 via the input lumen 520 and the outlet channel 524.

Air exhaled by the patient 500 enters the nasal cannula 2, 202,302, 402 via the first and second nasal inlet ports 16, 20 and is carried by the inlet channels 526 and outlet lumen 522 out of the cannula 402 via outlet port 12. The exhaled air is then carried by output conduit 512 to the monitor 516 to enable the composition of the exhaled air to be monitored, before being disposed of in any convenient manner.

Referring now to FIGS. 21 to 24, a cannula 602 according to a fifth embodiment of the invention is shown.

The cannula 602 comprises a body portion 4 having a first end 6 and a second end 8. The ends are spaced apart from one another by the body portion 4. The nasal cannula 602 comprises a first nasal input port 16 and a first nasal outlet port 18 extending from the body portion 4 of the cannula 602. The cannula 602 further comprises a second nasal inlet port 20 and a second nasal outlet port 22 each extending from the body portion 4 of the cannula 602. The first and second nasal input port 16, 20 are of the type shown in FIGS. 9 to 12 with respect to the third embodiment of the invention.

Figure 23:
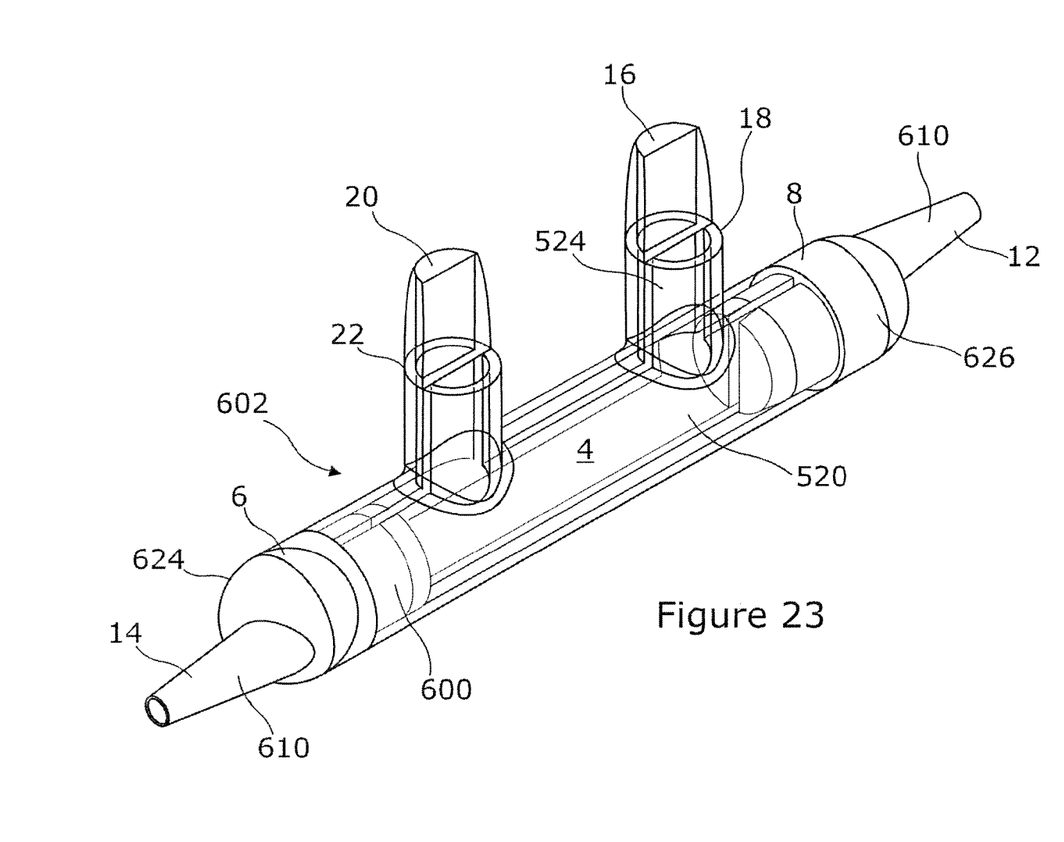
FIG. 23 is a schematic representation of a nasal cannula according to the fifth embodiment of the invention.
Figure 24:
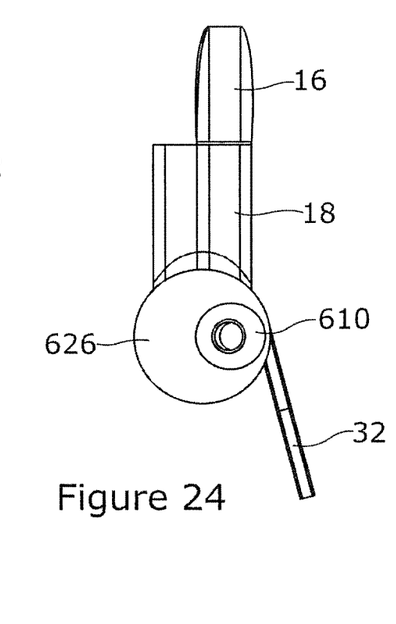
FIG. 24 is a view from one side of the cannula FIG. 23.

The nasal cannula 602 further comprises first and second end caps 624 and 626.

Figure 21:
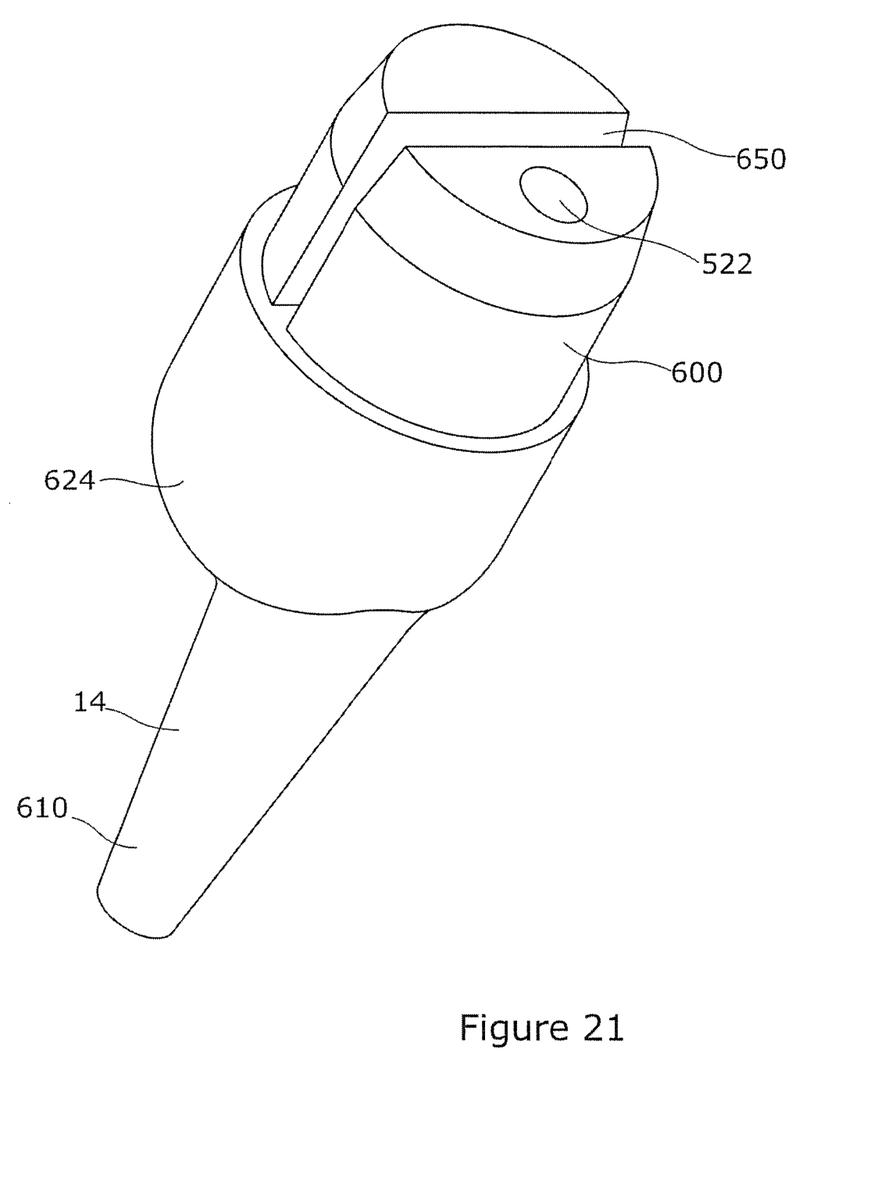
FIG. 21 is a schematic representation of an end cap forming part of a nasal cannula according to a fifth embodiment of the invention.
Figure 22:
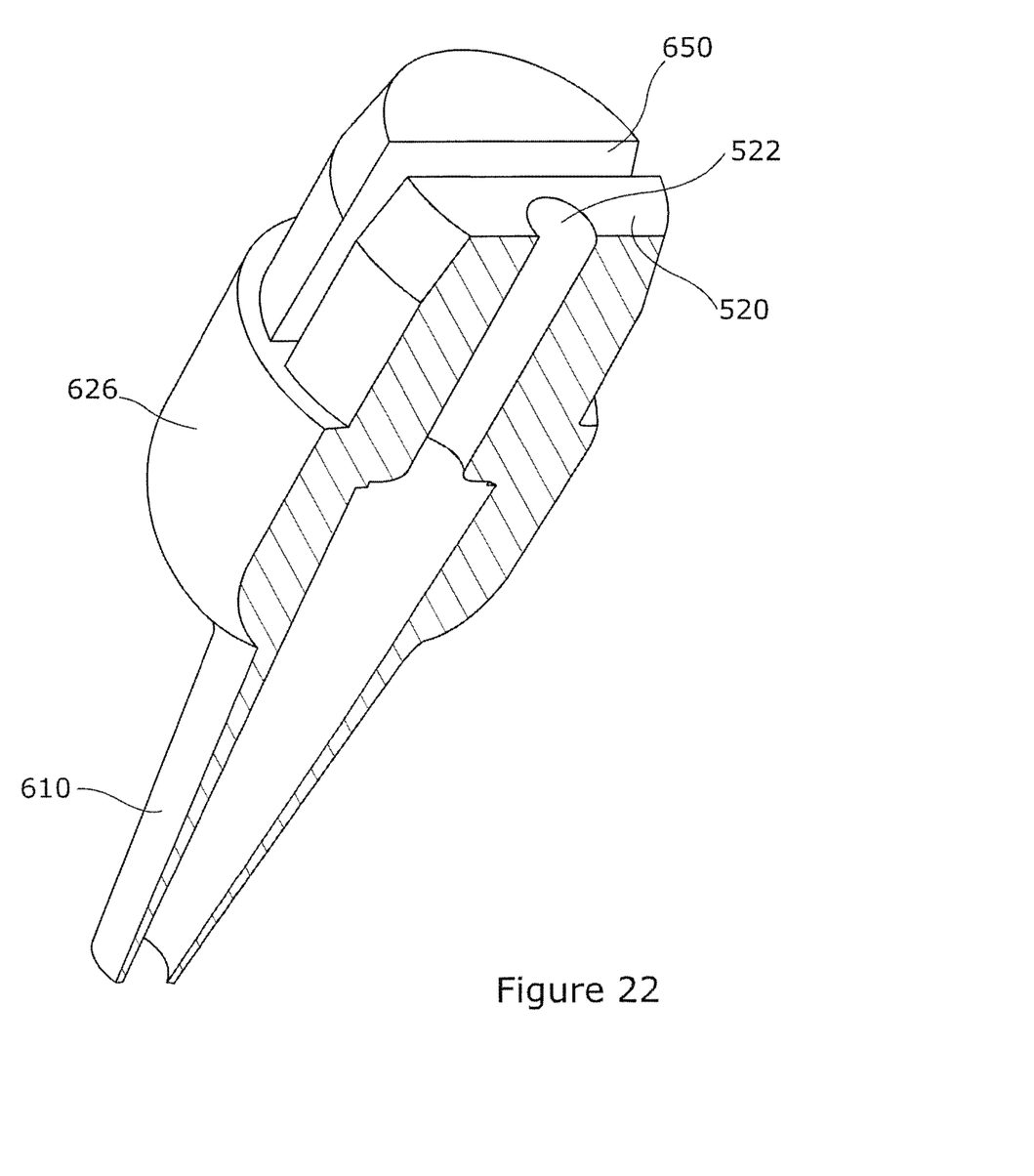
FIG. 22 is a cross-sectional representation of the end cap of FIG. 21.

The end caps 624, 626 are shown in more detail in FIGS. 21 and 22.

Each of the end caps 624, 626 comprises a spigot 600 which is sized and shaped so that it can inserted into the body portion 4 in order to attach a respective end cap 624, 626 to the body portion 4.

In this embodiment of the invention, each of the body fluid outlet port and the body fluid inlet port are in the form of a tube, or spike 610 extending from the respective end cap 624, 626.

The internal structure of the nasal cannula 602 is similar to that shown in FIGS. 19 to 20 with respect to the nasal cannula 302.

The end cap 624 comprises an output lumin 522, and the end cap 626 comprises an input lumin 520 (not shown).

The cannula 602 also comprises a divider 520 which extends through the body portion 4 and into each nasal projection. Each of the end caps 624, 626 comprises a slot 650 adapted to receive and support a divider 520 and hold the divider in place.

The internal structure shown particularly in FIGS. 19 and 20 may also be present in each of the other embodiments described and illustrated herein. In some embodiments however a different internal structure may exist.

The invention claimed is:

1. A nasal cannula comprising:
   a body portion, having a first end and a second end, the first and second ends being spaced apart from one another by the body portion;
   a body fluid outlet port formed at the first end, and a body fluid inlet port formed at the second end;
   first and second nasal projections extending from the body portion where the second nasal projection is spaced apart from the first nasal projection, the first nasal projection comprising a first nasal inlet port and a first nasal outlet port each spaced apart from the body portion, the second nasal projection comprising a second nasal inlet port and a second nasal outlet port each spaced apart from the body portion, the first and second nasal inlet ports being in fluid communication with the body fluid outlet port, and the first and second nasal outlet ports being in fluid communication with the body fluid inlet port
   a planar dividing wall extending through the body portion and substantially longitudinally at least partially through each nasal projection, where the planar dividing wall, together with the walls of the nasal projections and the walls of the body portion, separates the fluid communication between the first and second nasal inlet ports and body fluid outlet port from the fluid communication between the first and second nasal outlet ports and the body fluid inlet port; and
   first and second end caps at the first and second ends respectively, which first and second end caps are attachable to the body portion and comprise a slot adapted to receive and support the planar dividing wall, and wherein the body fluid outlet port is formed in the first end cap, and the body fluid inlet port is formed in the second end cap;
   wherein the first and second nasal inlet ports are positioned further from the body portion than the first and second nasal outlet ports.

2. The nasal cannula as claimed in claim 1, further comprising a plate extending from the body portion.

3. The nasal cannula as claimed in claim 1, wherein the body portion is substantially tubular.

4. The nasal cannula as claimed in claim 1, wherein the first and second end caps are each angled relative to the body portion.

5. The nasal cannula as claimed in claim 1, wherein the first and second end caps are each attached to the body portion by means of an adhesive.

6. The nasal cannula as claimed in claim 1, wherein the first and second end caps comprise first and second spigots respectively, which spigots are shaped to fit into a hollow end of the body portion.

7. The nasal cannula according to claim 6, wherein the body fluid inlet port and the body fluid outlet port each comprise an elongate portion extending from a respective end cap.

8. The nasal cannula as claimed in claim 1, comprising an inlet lumen extending from the body fluid inlet port to the first and second nasal outlet ports, and an outlet lumen extending from the first and second nasal inlet ports to the body fluid outlet port.

9. The nasal cannula as claimed in claim 8, wherein each nasal projection comprises an outlet channel forming part of the inlet lumen, and an inlet channel forming part of the outlet lumen, the inlet channel and the outlet channel each extending substantially longitudinally through a respective nasal projection.

10. The nasal cannula as claimed in claim 1, wherein each nasal projection comprises a proximal portion and a distal portion, wherein each inlet channel extends through the proximal portion and the distal portion of a respective nasal projection and each outlet channel extends through the proximal portion only of a respective nasal projection.

11. The nasal cannula according to claim 1, wherein in the body portion is made from a medical grade polymer, optionally PVC, optionally polyurethane.

12. The nasal cannula according to claim 1, wherein the first and second end caps are made from polycarbonate or ABS.

* * * * *